(12) United States Patent
Mukherjee et al.

(10) Patent No.: US 7,173,006 B2
(45) Date of Patent: Feb. 6, 2007

(54) DRUG COMPRISING SYNTHETIC PEPTIDE ANALOGS FOR THE TREATMENT OF CANCER

(75) Inventors: Rama Mukherjee, Sahibabad (IN); Anand C. Burman, Sahibabad (IN); Anu T. Singh, Sahibabad (IN); Manu Jaggi, Sahibabad (IN); Sudhanand Prasad, Sahibabad (IN); Sarjana Dutt, Sahibabad (IN)

(73) Assignee: Dabur Research Foundation, Ghaziabad (IN)

( * ) Notice: Subject to any disclaimer, the term of this patent is extended or adjusted under 35 U.S.C. 154(b) by 582 days.

(21) Appl. No.: 10/329,321

(22) Filed: Dec. 23, 2002

(65) Prior Publication Data

US 2004/0121950 A1    Jun. 24, 2004

(51) Int. Cl.
*A61K 38/00*    (2006.01)

(52) U.S. Cl. ........................................ 514/12; 530/300

(58) Field of Classification Search .................. 514/12; 530/300
See application file for complete search history.

(56) References Cited

U.S. PATENT DOCUMENTS 6,156,725 A * 12/2000 Mukherjee et al. ............ 514/12
6,492,330 B1 * 12/2002 Mukherjee et al. ............ 514/12
2003/0050233 A1 * 3/2003 Burman et al. ................ 514/12

* cited by examiner

*Primary Examiner*—Jeffrey Siew
*Assistant Examiner*—Laura B. Goddard
(74) *Attorney, Agent, or Firm*—Ladas & Parry LLP

(57) ABSTRACT

The present invention relates to a combination of peptides that may be used for treatment of cancer. The peptide combination competes for the binding of specific neuropeptides at the plasma membrane and thereby alters the levels of key intracellular molecules implicated in cell proliferation, resulting in a broad spectrum of anticancer activity. The invention also relates to pharmaceutical compositions containing a combination of such peptide analogs.

16 Claims, 1 Drawing Sheet

DRUG COMPRISING SYNTHETIC PEPTIDE ANALOGS FOR THE TREATMENT OF CANCER

FIELD OF INVENTION

The present invention relates to a combination of peptides that may be used for treatment of cancer. The peptide combination competes for the binding of specific neuropeptides at the plasma membrane and thereby alters the levels of key intracellular molecules implicated in cell proliferation, resulting in a broad spectrum of anticancer activity. The invention also relates to pharmaceutical compositions containing a combination of such peptide analogs.

BACKGROUND

Neuropeptides function peripherally as paracrine and endocrine factors to regulate diverse physiological processes and act as neurotransmitters and neuro-modulators. In a large majority of cases, the receptors which mediate signaling by neuropeptides are members of the superfamily of the G protein coupled seven membrane spanning receptors (Burbach and Meijer, Eur J Pharmacol, 227, 1–18, 1992). Neuropeptides have been documented to play important roles as autocrine/paracrine growth factors for human cancers (Rozengurt E, 1996, In Neuropeptides growth factors: Signaling pathways and role in cancer. In: Pusztai, L. L et al (editors)., Cell proliferation in cancer: Regulatory mechanisms of Neoplastic cell growth, Oxford, Oxford University press, page 247–259, 1996). The interruption of autocrine and paracrine neuropeptide signaling with specific antagonists or broad spectrum biased antagonists offer new therapeutic approaches to the treatment of cancer (Lynn E. H, Oncogene research, Vol 20, 1563–1569, 2001)

We have previously shown in our U.S. Pat. No. 6,156,725 and Australian Patent 707,158; (Mukherjee et al) that vasoactive intestinal peptide (VIP), somatostatin substance P and bombesin are secreted by some human tumor cells and that there are specific high affinity binding sites for these peptides on these cells. The four peptides were also shown to bind to tumor cells. The antagonist/analogs of these peptides were shown to have anti-proliferative activity on certain cancer cells, more specifically adenocarcinomas. A combination of the peptide antagonists/analogs was also shown to cause tumor regression in a nude mice xenograft model. It was hypothesized by us that there exists an autocrine mechanism for cell proliferation where the peptides are secreted by tumor cells and transduce cellular signals through specific cell surface receptors leading to cell proliferation. The analogs/antagonists to these peptides may then abrogate/block these cellular signals linked to proliferation. Further the antiangiogenic potential of the antagonist/analogs has also been described by us previously (Mukherjee et al; U.S. application Ser. No. 09/248,381 and PCT application WO 00/047221).

We have previously described in our U.S. patent (U.S. Pat. No. 6,316,414; Burman et al) novel peptides that are agonists to somatostatin and their use for the treatment of cancer. This invention particularly relates to the design and synthesis of novel analogs of somatostatin incorporating alpha, alpha-dialkylated amino acids in a site specific manner. The methods for the generation of these peptides, compositions containing the peptides and the pharmacological applications of these peptides especially in the treatment and prevention of cancer have also been described.

We have also described in our U.S. patent application Ser. Nos. (09/630,333, 09/630,345 and 09/629,642, Burman et al) novel antiproliferative analogs of VIP, bombesin and substance P that are useful in the treatment of cancer. These analogs incorporate $\alpha,\alpha$-dialkylated amino acids and show antiproliferative activity in a number of human tumor cell lines. Further, they caused partial tumor regression in nude mice xenografts when administered in a dose of approximately 1–25 microliter/mouse. Thus, when used individually, these peptides show moderate levels of cytotoxicity.

Neuropeptides and their analogs bind to specific high affinity transmembrane receptors on target cells to initiate a cascade of cytoplasmic signaling events. This includes the recruitment of several effector/adapter proteins initiating a cascade of protein-protein interactions. The binding of neuropeptides to their receptors causes the modulation of several cellular effector systems like adenylyl cyclase which cause alteration in the levels of second messenger molecules (Pimentel, In Growth factors and neoplasia, In Handbook of Growth factors, CRC Press, U.S.A, Vol 1, 329–337, 1994). The binding of peptide ligand to its receptor also causes the activation of intracellular protein kinases/phosphatases which are critical negative/positive regulators in the intracellular signaling pathways that result in growth factor specific cell responses like mitosis, differentiation, transformation or death. Several elements of this cascade have been directly/indirectly implicated in the malignant transformation and tumorogenesis of adenocarcinoma. The role of neuropeptides in cancer and cancer associated angiogenesis has been previously extensively reviewed. (Anticancer Res September–October 2000; 20(5A):3123–9); (Danesi R, Del Tacca M, Metabolism 1996 December; 45(8 Suppl 1): 49–50); (Woltering E A et al, J Surg Res 1991 March; 50(3): 245–251).

The adenocarcinomas express and secrete multiple growth factors viz. platelet derived growth factor (PDGF), epidermal growth factor (EGF) and transforming growth factor (TGF) alpha. The binding of growth factors to their respective receptors activates a cascade of intracellular pathways, specifically phosphorylation events mediated by protein kinases and phosphatases, which modulate the activity of a variety of cellular transcription factors. Aberrations in these signal-induced events are associated with cancer development and/or progression of cancer.

The cellular signaling mediated by receptors coupled to G proteins, as those for regulatory peptides are transduced through the cAMP-adenylyl cyclase system. The mitogenic response of the cells to growth factors and regulatory peptides is influenced by intracellular concentrations of cAMP, which in turn activates the cAMP dependent protein kinases (PKA), cAMP cooperates with a variety of hormones and growth factors to synergistically stimulate the proliferation of different type of eukaryotic cells.

The receptor tyrosine kinases (RTK) are transactivated by G protein coupled receptors (GPCR). Platelet derived growth factor (PDGF), epidermal growth factor (EGF) and insulin like growth factor 1 (IGF1) are tyrosine phosphorylated subsequent to GPCR activation. The phosphorylated growth factors in turn recruit multiple accessory proteins to activate the mitogen activated protein kinases (MAPK). Human adenocarcinomas have increased constitutive MAPK activity (Ostrowski et al, Br. J Cancer Vol 78, 1301–1306, 1997), and the blockade of this protein kinase suppresses tumour growth in vitro and in vivo (Sebolt-Leopold et al, Nature Medicine, Vol 5, 810–816, 1999). The MAP Kinase pathway is a crucial convergence point for many cytoplasmic signaling networks. MAP kinases form a family of Ser/Thr kinases, which can be activated by cellular growth factors. MAP Kinase lies downstream of the Ras-Raf oncogenic pathway and its activation leads to phosphorylation of nuclear transcription factors resulting in cell proliferation (Ostrowski et al., Br. J Cancer Vol 78, 1301–1306, 1997).

Membrane associated tyrosine phosphatases dephosphorylate specific targets, thus functionally opposing the action of tyrosine kinases. Inhibition of tyrosine phosphatase reversibly induces transformation of cultured cells in a dose dependent manner in vitro. Induction of tyrosine phosphatases in cancer cells leads to cell differentiation and reversal of transformed phenotype.

The p53 tumor suppressor protein plays a key role in the control of the normal cell cycle & apoptotic signalling. p53 gene mutations occur in approximately half of all malignancies from a wide variety of human tumors and are associated with poor prognosis and treatment (Kirch & Kastan, J. Clin Oncology, Vol 16, 3158–3168, 1998). Over expression of wild type p53 in cells induces cell cycle growth arrest, which in specific cases results in apoptosis.

Bcl-2 is the first member of a family of proteins shown to prevent death that is either p53 dependant or p53 independent (Peled et al, Cancer research, 56, 2148–2156, May 1, 1996). Overproduction of the bcl-2 protein also prevents cell death induced by nearly all cytotoxic anticancer agents frequently contributing to treatment failures in patients with several types of cancers (Reed et al, J. Cell Biochem, Vol 60, 23–32, 1996). The apoptotic fragmentation of the DNA is brought about by the sequential activation of the family of caspases.

SUMMARY OF INVENTION

In our present application, we have used a combination of peptide analogs, which as compared to individual peptides, causes a significantly higher cytotoxicity to tumor cells. This led us to investigate the key intracellular signaling molecules that were altered by the peptide combination.

The peptide analogs in the combination compete with the receptors for the native peptides at the plasma membrane thereby synergistically down-regulating the intracellular signals converging at specific molecules stimulated by these pro-proliferative peptides resulting in inhibition of tumor or cancer cell proliferation.

We investigated the effects of the peptide combinations for their modulation of specific intracellular molecules in adenocarcinoma cells. The Epidermal growth factor (EGF) dependent proliferation of the cancer cells, the intracellular cAMP levels, the Mitogen activated protein kinase (MAPK) activity and the tyrosine phosphatases, were modulated by the peptide combination of this invention. Further, the peptide combination induced p53 expression, downregulated the levels of the antiapoptotic protein bcl2 and activated Caspase 3, thus triggering the apoptotic cell death in adenocarcinomas. The induction of the tumor suppressor protein p53 by this combination is a novel property of this combination, not reported earlier. Additionally the combination is also antiangiogenic as it inhibits "tube-like structure" formation and migration of endothelial cells concomitantly with a decrease in the levels of VEGF. Thus, the combination of peptides blocks several of the pathways implicated in cell proliferation by altering the levels of key molecules involved and is therefore able to cause not only significantly higher cell death but also displays a broader spectrum of anticancer activity. The peptide combination causes significant reduction in cAMP levels in adenocarcinomas of the stomach and breast. It inhibits epidermal growth factor (EGF) dependent proliferation in the pancreatic cancer cells. The peptide combination causes the induction of active caspase-3 in ovarian cancer cells, and it causes decrease in levels of VEGF in breast cancer cells. Therefore, having conducted several experiments, we have optimized a combination of peptides with high cytotoxic and broad-spectrum activity. The anticancer effect of the present invention is mediated by altering the multiple cellular pathways in the neoplastic cells thereby leading to apoptosis and anti-angiogenic activity.

The present invention relates to a composition useful for killing or inhibiting the growth and/or multiplication of tumor and/or cancer cells. The composition may suitably comprise, consist of, or consist essentially of a therapeutically effective combination of a peptide analog of somatostatin, a peptide analog of a vasoactive intestinal peptide, a peptide analog of bombesin and a peptide analog of substance P. In a preferred embodiment, a pharmaceutically effective carrier, diluent, or solvent is used with the peptide analogs. The invention also provides a method of treatment for humans, mammals or other animals suffering from cancer and cancer associated angiogenesis and metastasis. The method may suitably comprise, consist of, or consist essentially of administering a therapeutically effective dose of the composition so as to inhibit tumor or cancer associated angiogenesis or metastasis and to kill, inhibit the growth or inhibit the multiplication of cancer or tumor cells by inducing apoptosis. Another aspect of the invention provides a method for treating a mammal (including a human being) afflicted with cancer. The methods of this invention comprise, consist of, or consist essentially of administering systematically to the mammal a therapeutically effective combination of peptides.

DETAILED DESCRIPTION OF THE INVENTION

Figure 1:
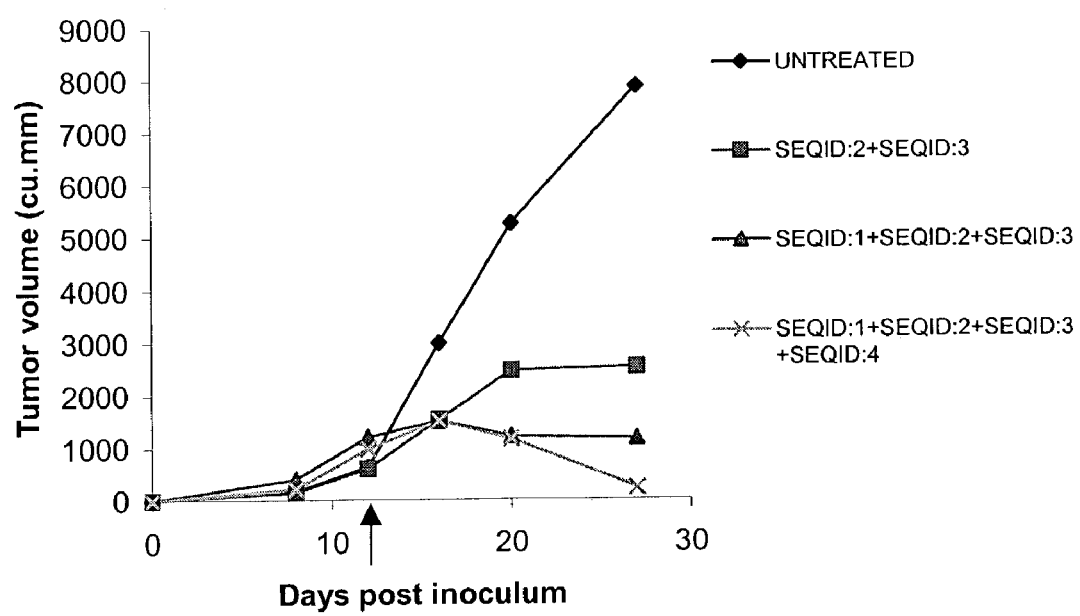
FIG. 1 shows in viva antitumor activity on subcutaneous administration of the peptide combination on PTC xenografts.

This invention comprises, consists of, or consists essentially of a composition of combination of 4 PEPTIDES of SEQ ID NO: 1, SEQ ID NO: 2, SEQ ID NO: 3 and SEQ ID NO: 4. The combination consists of:

SEQ ID NO: 1
SEQ ID NO: 2
SEQ ID NO: 3
SEQ ID NO: 4

The amino acid sequences represented by SEQ ID NO: 1, SEQ ID NO: 2, SEQ ID NO: 3 and SEQ ID NO: 4. are described below. One or more of the pharmaceutically acceptable salt of SEQ ID: 1, SEQ ID NO: 2, SEQ ID NO: 3 and SEQ ID NO: 4 can be used in place of the respective SEQ ID: 1, SEQ ID NO: 2, SEQ ID NO: 3 and SEQ ID NO: 4. The concentration of each peptide in the combination is $10^{-6}$ to $10^{-10}$M, preferably $10^{-8}$ to $10^{-9}$M.

The sequence of the VIP receptor binding inhibitor is:

Leu-Met-Tyr-Pro-Thr-Tyr-Leu-Lys-OH (SEQ ID NO:1) which is described in our U.S. patent application Ser. No. 09/630,345

The sequence of Bombesin antagonist is:
D-Phe-Gln-Trp-Ala-Val-Aib-His-Leu-NH$_2$ (SEQ ID NO: 2) which is described in our U.S. patent application Ser. No. 09/630,333.

The sequence of Substance P antagonist is:
D-Arg-Pro-Lys-Pro-D-Phe-Gln-D-Trp-Phe-D-Trp-Leu-Ac5c-NH$_2$ (SEQ ID NO:3) which is described in our U.S. patent application Ser. No. 09/629,642.

The sequence of Somatostatin analogue is:
D-Phe-Cys-Tyr-D-Trp-Orn-Thr-Pen-Thr-NH$_2$ (SEQ ID NO:4) (There is a disulphide bond between Cys and Pen amino acids) which is described in our U.S. Pat. No. 6,156,725 (Mukherjee et al)

The methods of this invention comprise, consist essentially or consist of administering to a human or animal, preferably a mammal, a therapeutically effective combination of this invention. The combinations of this invention can be used to kill or inhibit the multiplication of tumor cells or cancer cells. The combinations are especially effective in treating breast, ovarian, colon, lung, pancreatic, prostate, stomach and oral cancer and in treating skin fibroblasts. The combinations of this invention can be used to down regulate epidermal growth factor dependent proliferation, intracellular levels of cAMP, intracellular activity of mitogen activated protein kinase (MAPK); and upregulate intracellular activity of tyrosine phosphatase in various cancer cell types. They can also be used to induce wild p53 protein, caspase enzyme activity and inhibit bcl2 protein, and inhibit secretion of vascular endothelial growth factor (VEGF) in these cancer cell types.

The ratio of peptides in the formulation can vary such that the weight of one peptide may be between 1 to 3 times the weight of another peptide. The total weight of a single dose is between 0.01 to 50.0 mg. This conforms to a dose of 0.05–500 microgram/Kg. body weight of the human or animal. These peptides have their best in vitro or systemic biological activity (anticancer) when their individual concentrations range between $10^{-6}$ M to $10^{-10}$ M (preferably $10^{-8}$ M to $10^{-9}$ M). It is not necessary that the weight of all the peptides in the dose should be the same. The weight of the peptide in a dose would depend upon many factors such as (i) bioavailability of peptide, (ii) half-life of peptide, (iii) number and affinity of receptors for a particular peptide on tumor and (iv) type of tumor or cancer to be treated.

An effective dose of the combination ranges from 0.05–500 microgram/Kg. body weight of the mammal, with the dose dependent on inter alia the effects sought, the manner of administration, the peptide selected, and the cancer being treated. Systemic administration refers to oral, rectal, nasal, transdermal, and parentral (i.e., intramuscular, intravenous, and subcutaneous). In accordance with good clinical practice, it is preferred to administer the composition at a dose that will produce anticancer effects without causing undue harmful side effects. The composition may be administered either alone or as a mixture with other therapeutic agents such as 5-fluorouracil, methotrexate, etoposide, paclitaxel, taxotere, doxorubicin, daunarubicin, vincristine, vinblastine and other such anticancer drugs.

The composition may optionally and preferably contain pharmaceutically acceptable diluents, excipients, solvents, binders, stabilizers, and the like. Such diluents may include: rpmi 1649, buffered saline, isotonic nacl, ringer's solution, water, distilled water, polyethylene glycol (neat or in water), 2% tween in water, dimethyl-sulfoxide to 50% in water, propylene glycol (neat or in water), phosphate buffered saline, balanced salt solution, glycerol, and other conventional fluids that are suitable for intravenous administration. Pharmaceutical composition which provide from about 0.5 to 20 mg (preferably 0.5 to 10.0 mg of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration Pharmaceutical compositions which provide 0.01 to 50.0 mg of the combination per unit dose are preferred and are conventionally prepared as tablets, lozenges, capsules, powders, aqueous or oily suspensions, syrups, elixirs, and aqueous solutions. The nature of the pharmaceutical composition employed will, of course, depend on the desired route of administration.

An effective amount means that amount of a peptide, combination of peptides or composition comprising, consisting essentially of or consisting of peptides that will elicit the biological medical response of a tissue, system cell, animal or human that is being sought.

A PubMed search of the National Library of Medicine was carried out to determine the relevance of cell lines used by us for determining the anticancer activity of the peptides. While HT29 (human colon) showed 2021 "hits" when searched with reference to cancer, other human cancer cell lines used by us also showed large number of hits (6848 for K562, 2532 for MOLT-4, 542 for DU145, 1063 for MCF-7 and 182 for PA-1). This clearly shows the extensive use of these cell lines in cancer research. Further, it is a common and standard practice and norm for testing molecules for anticancer activity in vitro on human tumor cell lines. (Br J Cancer. 2001 May 18; 84(10):1289–90 (Flasks, Fibres and Flanks—Preclinical tumor models for predicting clinical antitumor activity). The authors report that in vitro activity against 6 or more lung or breast cancer cell lines does predict xenograft activity against these tumor types. In articles "Semin Oncol 1992 December; 19(6):622–38 (The National Cancer Institute: cancer drug discovery and development program) and "Jpn J Antibiot December 1992; 30 Suppl: 35–40 (Antitumor screening procedures of the National Cancer Institute)" extensive use of human tumor cell lines for identification of potential cytotoxic drugs is described.

The present invention is further described in detail with reference to the following examples, which are given for the purpose of merely illustrating the invention without limiting it.

EXAMPLE 1

Synthesis of Peptides

The peptides in the present invention have been generated by solid phase technique following the Fmoc strategy, on a semi automatic peptide synthesizer (CS Bio, Model 536), using optimum side chain protection. The peptides were assembled from C-terminus to N-terminus. Peptides amidated at the carboxy-terminus were synthesized using the Rink Amide resin and free carboxy terminus peptide using Wang Resin.

After the assembly of the peptide was completed, the amino-terminal Fmoc group was removed and then the peptide-resin was washed with methanol and dried. The peptides were then deprotected and cleaved from the resin support by treatment with trifluoroacetic acid, crystalline phenol, ethanedithiol, thioanisole and de-ionized water for 1.5 to 5 hours at room temperature. The crude peptide was obtained by precipitation with cold dry ether. It was further dissolved in water and lyophilized.

The resulting crude peptide was purified by preparative high performance liquid chromatography using a C-18 reverse phase column on a Preparative HPLC system using a gradient of 0.1% TFA in acetonitrile and water. The eluted fractions were reanalyzed on analytical HPLC system. Acetonitrile was evaporated and the fractions were lyophilized to obtain the pure peptide. The identity of each peptide was confirmed by mass spectroscopy. The peptides yielded as trifluoracetate salt. The peptides may contain other pharmaceutically acceptable salts. Salts encompassed within the term "pharmaceutically acceptable salt" refer to nontoxic salts of the compounds of this invention. Representative salts and esters include the following: acetate, ascorbate, benzoate, citrate, oxalate, stearate, trifluoroacetate, succinates, tartarate, lactate, fumarate, gluconate, glutamate, phosphate/diphosphate, valerate and the like.

The following abbreviations are used for uncommon amino acids:

Orn=Ornithine

Pen=Penicillamine

Aib=α-Aminoisobutyric acid

Ac5c=1-Aminocyclopentane caboxylic acid

EXAMPLE 2

The Combination was Prepared in the Following Way

A stock solution for each of the four peptides (SEQ ID NO:1, SEQ ID NO: 2, SEQ ID NO:3 and SEQ ID NO: 4) is prepared with a pH of approximately 3.5 to 7.0 but preferably 4.0 to 5.5. Although sterile phosphate buffered saline was used to prepare each stock solution for the testing described in the following example, other diluents may be used such as buffered saline, isotonic NaCl, Ringer's solution, water, distilled water, polyethylene glycol (neat or in water), Tween in water, dimethylsulfoxide upto 50% in water, propylene glycol (neat or in water), phosphate buffered saline, balanced salt solution, glycerol, and other conventional fluids that are suitable for parentral administration. To obtain a pH in the range of approximately 3.5 to 7.0, for each stock solution, the pH can be adjusted by using 1N HCl for lowering the pH or 1N NaOH for raising the pH, although other buffers such as citrate buffer, phosphate buffer and the like or other conventional agents for adjusting the pH can be used. The stock solution of each peptide is then mixed in appropriate dilutions so as to give a final concentration of $10^{-6}$ to $10^{-10}$ M but more preferably in the range of $10^{-8}$ to $10^{-10}$M and still more preferably at $10^{-8}$M. A stock solution for the pharmaceutically acceptable salts is prepared in the same way.

Formulation of a Dose of the Combination for Parentral Administration

A dose of the formulation of combination was prepared in the following way. A stock solution of each of the four peptides SEQ ID NO:1, SEQ ID NO:2, SEQ ID NO:3 and SEQ ID NO:4 was first prepared using sterile phosphate buffered saline with an approximate pH of 4.0 to 5.5. Aliquots of the stock solutions of the peptides were mixed together to prepare formulations containing combinations of two peptides, formulations containing three peptides or formulations containing four peptides. The ratio of peptides in the formulations can vary such that the weight of one peptide may be between 1 to 3 times the weight of another peptide. More preferably, the ratio of the four peptides SEQ ID NO:1, SEQ ID NO:2, SEQ ID NO:3 and SEQ ID NO:4 should be 3:1:1:2 (w/w). The total weight of a single dose is between 0.01 to 50.0 mg. This conforms to a dose of 0.05–500 microgram/Kg. body weight of the mammal. Preferably, the weight of the four peptides SEQ ID NO:1, SEQ ID NO:2, SEQ ID NO:3 and SEQ ID NO:4 in the dose should be in the ratio of 3:1:1:2. These peptides have their best in vitro or systemic biological activity (anticancer) when their individual concentrations range between $10^{-6}$ M to $10^{-10}$ M (preferably $10^{-8}$ M to $10^{-9}$ M, more preferably $10^{-8}$M.). To achieve therapeutically effective systemic concentrations, a dose of 0.05–500 microgram/Kg.B.Wt of the mammal needs to be administered. Further, it is not necessary that the weight of all the peptides in the dose should be the same. The weight of the peptide in a dose would depend upon many factors such as (i) bioavailability of peptide, (ii) half-life of peptide, (iii) number and affinity of receptors for a particular peptide on tumor and (iv) type of cancer or tumor to be treated.

EXAMPLE 3

Primary human colon adenocarcinoma, PTC and squamous cell carcinoma, KB were cultured in RPMI 1640 medium supplemented with 2 mM glutamine, 25 mM HEPES, 100 u/ml penicillin, 50 micromolar/ml streptomycin, 40 micromolar/ml gentamycin and 10% FCS. The cells were maintained at 37° C. in a humidified atmosphere containing 5% $CO_2$ All binding assays were performed at 4° C. $^{125}I$ labeled VIP, Bombesin, Somatostatin, Substance P, and TGFα each of specific activity 2000 Ci/mmol were obtained from DuPont NEN, USA. The assay was carried out on intact cells as described by (Qin et al., 1995. Briefly, $5\times10^4$ cells were seeded per well of a 24 well culture plate and allowed to adhere overnight. The cells were washed twice with ice cold Binding buffer (10 mM $MgCl_2$, 1% BSA, 1 mM EGTA, 0.25 mM PMSF and 10 micromolar/ml aprotinin in RPMI 1640). Cells were incubated with 3 nM of either VIP, Bombesin or Substance P or TGFα or with 2 nM of Somatostatin in the presence or absence of various concentrations of cold peptide combination and allowed to incubate for 2 hrs. at 4° C. The cells were subsequently washed thrice with ice cold Binding buffer to remove unbound radioligand and lysed with 20 mM Tris-HCl buffer, pH 7.4, containing 1% SDS. The radioactive counts in the cell lysate were measured using a gamma counter (LKB Wallace, Finland). Nonspecific binding was determined in the presence of 1 μM of the native peptide. The counts were processed using the EBDA Biosoft program to obtain Kd and Bmax (pmol/mg cellular protein) values.

Cold competition studies with peptide combination (SEQ ID NO:1; SEQ ID NO:2, SEQ ID NO:3 and SEQ ID NO:4) show that the constituent peptides of the drug are able to bind the neuropeptide receptors for VIP, Somatostatin, Bombesin and Substance P on PTC cells. The peptide combination did not displace the binding of TGF α from its receptors, even when it was added in 30000 fold concentration compared to that of TGF α. The drug was able to displace the native peptides from their respective receptors in a dose dependent manner (Table 1).

TABLE 1

Percent Inhibition Of The Binding Of The Native Neuropeptides
On PTC By Peptide Combination
Fold excess of cold Peptide combination

| Neuropeptide | 400 fold (1.2 micromolar) | 1000 fold (3 micromolar) | 30,000 fold (90 micromolar) |
|---|---|---|---|
| VIP | 2.6% | 35.87% | 94.01% |
| Somatostatin | 20.31% | 42.91% | 96.6% |
| Bombesin | 7.89% | 39.08% | 93.13% |
| Substance P | 5.06% | 27.71% | 97.52% |
| TGF ∝ | Nil | Nil | 4.5% |

Peptide combination was able to significantly inhibit the binding of the radiolabeled native peptides at a concentration 1000 fold higher than the native peptide and less than 10% residual binding remained in all cases at 30,000 fold excess.

Cold competition studies with peptide combination on KB cells show that the constituent peptides of the drug are able to bind the neuropeptide receptors for VIP, Somatostatin, Bombesin and Substance P. The drug was able to displace the native peptides from their respective receptors in a dose dependent manner as seen for PTC (Table 2). The peptide combination did not displace the binding of TGF ∝ from its receptors, even when it was added in 30000 fold concentration compared to that of TGF ∝.

Peptide combination was observed to inhibit the binding of the radio-labeled native peptides to KB cells at a concentration of 1000 fold excess and less than 10% specific binding remained in all cases at 30,000 fold excess

TABLE 2

Percent Inhibition Of The Binding Of The Native Neuropeptides
On KB By Peptide Combination
Fold excess of cold peptide combination

| Neuropeptide | 400 fold (1.2 micromolar) | 1000 fold (3 micromolar) | 30,000 fold (90 micromolar) |
|---|---|---|---|
| VIP | 8.64% | 50.4% | 93.17% |
| Somatostatin | 12.9% | 45% | 97.8% |
| Bombesin | 19.16% | 62.54% | 86.3% |
| Substance P | 13.29% | 38.5% | 98.8% |
| TGF ∝ | Nil | Nil | 4.25% |

These results suggest that the peptide derivatives incorporated in peptide combination remain functional in the combined formulation as well and are able to competitively inhibit the binding of physiologically relevant concentrations of the native neuropeptides. Further the peptide combination does not compete for the binding of the growth factors at the plasma membrane viz. as for TGF ∝. The data suggests that the displacement of specific proproliferative neuropeptides from their receptors at the plasma membrane, may synergistically downregulate the intracellular signals stimulated by these pro-proliferative peptides, without altering the binding of the growth factors and indirectly leads to an inhibition of tumor or cancer cell proliferation.

EXAMPLE 4

Cytotoxic Effect of the Combination on Human Tumor Cell Lines

Experiments were conducted to study the cytotoxic effect of the combination on 23 human tumor cell lines using the three-day MTT cytotoxic assay. These cell lines were K562 (human leukemia), MOLT-4 (human lymphoma), L132 (lung), A549 (human lung carcinoma), MCF-7 (breast), HBL100 (breast), MDA.MB.453 (human breast), SW620 (colon), PTC (colon), CoLo205 (colon), HT29 (colon), CaCO.2 (human colon), HuTu80 (human duodenum), and Hu746T (human stomach). Briefly, cells from the 23 human tumor cell lines were incubated in a 96-well culture plate (approximately 50,000 cancer cells in each well) for 72 hours at 37° C. in a $CO_2$ incubator. The combination SEQ ID NO: 1+SEQ ID NO: 2+SEQ ID NO: 3+SEQ ID NO: 4, all at $10^{-8}$ M concentration (20 ul per well) was added to the wells of all the treated samples at time 0, 24, and 48 hours. The controls were cells from 23 tumor cell lines that were not treated with the combination. At the end of 72 hours, stock MTT solution was added to each well, and incubation continued for one additional hour. After adding SDS-0.01N HCl, the plate was read at 540 nm. The percent cytotoxicity caused by the combination in each of the 23 cell lines is listed in Table-3.

TABLE 3

Percentage Cytotoxicity Caused By Peptide Combination
In 21 Human Tumor Cell Lines

| Cell line | Tumor type | Percent Cytotoxicity |
|---|---|---|
| Colon | PTC | 94.2 ± 3.1 |
| | CoLo205 | 80.1 ± 6.3 |
| | HT29 | 41.4 ± 2.7 |
| | SW620 | 33.2 ± 4.7 |
| | CaCO.2 | 79.2 ± 3.4 |
| Lung | L132 | 36.2 ± 4.3 |
| | A549 | 15.2 ± 4.8 |
| Breast | HBL100 | 52.5 ± 3.8 |
| | MDA.MB.453 | 47.2 ± 2.2 |
| | MCF-7 | 34.6 ± 5.8 |
| Leukemia | MOLT-4 | 81.3 ± 4.2 |
| | K562 | 41.9 ± 4.8 |
| Glioblastoma | U87MG | 84.2 ± 2.4 |
| | U373MG | 88.3 ± 3.1 |
| Pancreas | MiaPaCa.2 | 85.4 ± 2.9 |
| Prostate | DU145 | 46.2 ± 3.1 |
| Cervical | HeLa | 33.1 ± 1.8 |
| Ovary | PA-1 | 28.4 ± 4.1 |
| Stomach | HuTu80 | 92.1 ± 2.2 |
| Duodenum | Hs746T | 9.4 ± 3.7 |
| Oral | KB | 70.0 ± 2.7 |
| SK.MEL.28 | Melanoma | Not active |
| SKO.007 | Myeloma | Not active |

EXAMPLE 5

Effect of Peptide Combination on Camp Levels in Breast Cancer Cells

Enzyme linked sandwich immunosorbent assay was carried out on breast cancer cells (MCF7) to study the modulation in levels of cAMP upon treatment with the peptides and their combinations. The cells were cultured in sterile 6 well plates at a density of $0.5 \times 10^6$/well in DMEM supplemented with 10% FCS, and allowed to adhere overnight. The medium was changed to DMEM and the cells were treated with appropriate concentrations of the peptide and its combinations, as shown in Table III, for 30 minutes, such that in each case the final peptide concentration was $10^{-9}$M.

The cells were co-incubated with Forskolin at a concentration of 1 micromolar. The cells were scraped using a cell scraper and pelleted. The cell pellet was suspended in appropriate resuspension buffer (50 mM Tris, containing EDTA, 0.2 mM phenyl methyl sulfonyl fluoride (PMSF), 1 ug/ml pepstatin and 0.5 microgram/ml leupeptin adjusted to pH 7.4). The cell extracts were transferred to microcentrifuge tubes and centrifuged for 5 minutes at 10000×g. cAMP standards ranging in concentrations from 200 units/ml to 0 units/nil were prepared immediately prior to the start of the assay. Fluorescein isothiocyanate (FITC) conjugated monoclonal antibody directed to cAMP was added to microtitre wells precoated with primary monoclonal antibody against cAMP. 50 ul of sample lysates, and cAMP standards were added in duplicates in the microtitre wells containing both the monoclonals to cAMP. The wells were incubated at room temperature for 2 hours. The microtitre wells were washed three times with appropriate wash buffer (PBS 50 mM, with Tween 0.5%) and the appropriate dilution of anti FITC horse radish peroxidase conjugate was added and incubated for 30 minutes. The microtitre wells were washed thrice with the wash buffer and subsequently with distilled water. Tetramethylbenzidine was added to each well and incubated in dark for 30 minutes at room temperature. The absorbance was measured in each well at dual wavelength of 450/595 nm within 30 minutes of the addition of stop solution and the amount of cAMP present in the cell samples calculated.

The intracellular levels of cAMP on treatment with peptide sub-combinations was downregulated by 30 minutes of the treatment. Table 4 shows percentage inhibition in the levels of cAMP following treatment with subcombinations on MCF 7 cells (breast cancer cells). The maximum inhibition in the intracellular levels of cAMP was seen with the four peptide combination of SEQ ID NO: 1+SEQ ID NO: 2+SEQ ID NO:3+SEQ ID NO:4.

TABLE 4

Camp Levels Expressed As Percent Of The Control Values In Breast Cancer Cells Treated With The Peptide Combination

| S. No. | PEPTIDE (combinations) | cAMP (% Of Control) |
|---|---|---|
| 1 | SEQ ID NO: 1 | 25.2 ± 4.5 |
| 2 | SEQ ID NO: 2 | 15.4 ± 3.0 |
| 3 | SEQ ID NO: 3 | 13.3 ± 4.0 |
| 4 | SEQ ID NO: 4 | 12.9 ± 5.0 |
| 5 | SEQ ID NO: 1 + SEQ ID NO: 2 + SEQ ID NO: 4 | 13.7 ± 5.5 |
| 6 | SEQ ID NO: 1 + SEQ ID NO: 2 + SEQ ID NO: 3 + SEQ ID NO: 4 | 5.7 ± 6.0 |

EXAMPLE 6

Effect of Peptide Combination on Epidermal Growth Factor Dependent Proliferation in Pancreatic Cancer Cells (Miapaca2)

Pancreatic cancel cells (MiaPaCa2) were cultured in 96 well culture plates at a density of 10000 cells /well in DMEM supplemented with 10% FCS, and allowed to adhere overnight. The medium was changed to DMEM and the cells were treated with recombinant Epidermal growth factor (EGF) in a concentration ranging from 5 nM to 1 micromolar. The cells were incubated for a cumulative period of 72 hours. EGF was added to the cells once every 24 hours. The control cells were not treated with EGF. The survival fraction of the cells treated with EGF was compared to that in the untreated cells by the MTT assay.

The assay was terminated by adding 100 microgram (20 microliter) of MTT to each well, then incubating for additional one hour, and finally adding 50 microliter of 10% SDS-0.01N HCl to each well to lyse the cells and dissolve formazan. After incubating for one hour, the plate was read spectrophotometrically at 540 nm and the cell survival fraction calculated. The optimal concentration of EGF causing proliferation of the pancreatic cells was obtained. The pancreatic cancer cells were treated with the optimal concentration of EGF (5 nM) and the peptide subcombinations shown in Table 5, for 72 hours, such that in each case the final peptide concentration was $10^{-9}$M.

The peptide combination and EGF were added every 24 hours. The fraction of surviving cells was calculated for each peptide combination by the MTT assay described above. Table 5 below shows the survival fraction of the cells treated with EGF and different peptide combinations.

The Epidermal growth factor dependent cellular proliferation was abrogated by the peptide combinations to varying extents in vitro. This inhibition was specific for EGF as the experiments were carried out in medium free of any other growth factors. Table 5 shows the survival fraction of cells treated with varying peptide combinations expressed as a percent of control untreated cells. The maximal inhibition of the proliferation was blocked by four peptide combination of SEQ ID NO:1+SEQ ID NO: 2+SEQ ID NO:3+SEQ ID NO:4.

TABLE 5

Percent Surviving Cells In Human Pancreatic Cells Treated With Epidermal Growth Factor & Peptide Combinations

| S. NO. | PEPTIDE COMBINATIONS | Survival fraction of cells |
|---|---|---|
| 1 | SEQ ID NO: 1 | 90.6 ± 5.0 |
| 2 | SEQ ID NO: 2 | 80.4 ± 6.0 |
| 3 | SEQ ID NO: 4 | 96.9 ± 5.5 |
| 4 | SEQ ID NO: 3 | 75.2 ± 4.0 |
| 5 | SEQ ID NO: 2 + SEQ ID NO: 1 | 55.9 ± 5.6 |
| 6 | SEQ ID NO: 1 + SEQ ID NO: 2 + SEQ ID NO: 4 | 60.4 ± 6.7 |
| 7 | SEQ ID NO: 1 + SEQ ID NO: 2 + SEQ ID NO: 3 + SEQ ID NO: 4 | 10.5 ± 9.0 |

EXAMPLE 7

Effect of Peptide Combination on Tyrosine Phosphatase Activity in Pancreatic Cancer Cancer Cells The quantitation of tyrosine phosphatase was carried out colorimetrically by using their synthetic biotin labeled tyrosine phosphorylated peptide substrates. The enzyme reaction was quenched by the addition of a specific inhibitor, and the phosphorylated and dephosphorylated substrate is immobilized by binding to the streptavidin coated microtitre plate. The fraction of the unmetabolized substrate is determined by its anti phospho tyrosine antibody directly conjugated to peroxidase.

The cells were cultured in sterile 6 well plates at a density of $0.5 \times 10^6$/well in DMEM supplemented with 10% FCS, and allowed to adhere overnight. The medium was changed to DMEM. The cells were treated with appropriate concentrations of the peptide and their combinations shown in Table 6, for 30 minutes, such that in each case the final peptide concentration was $10^{-9}$M.

The cells were lysed in appropriate lysis buffer (50 mM Tris, containing EDTA, 0.2 mM PMSF, 1 microgram/microliter pepstatin and 0.5 microgram/microliter leupeptin adjusted to pH 7.4). The cell extracts were transferred to microcentrifuge tubes and centrifuged for 5 minutes at 10000×g.

The quantitation of phosphatase enzyme activity was performed with 30 microliter of specific substrates and the reaction was quenched with the addition of 100 micromolar sodium orthvanadate. The reaction mixture was added to streptavidin coated microtiter plate. The wells were washed thoroughly and 75 microliter of Anti-Phospho Tyrosine antibody was added to the plate. After 3 washings, 100 microliter of the substrate POD was added to the wells, and the absorbance was read at 405 nM.

The peptide combination induced tyrosine phosphatase activity in within 30 minutes in pancreatic cancer cells. Table-6 shows show percentage induction of tyrosine phosphatase activity following treatment with the subcombinations on pancreatic cancer cell line (MiaPaCA2). The maximum induction of tyrosine phosphatase 150% in pancreatic cancer cells (Mia PaCa2) occurred in the four peptide combination of SEQ ID NO:1, SEQ ID NO:2, SEQ ID NO:3 and SEQ ID NO:4.

TABLE 6

Induction Of Tyrosine Phosphatase Activity Expressed As Percent Of The Control Values In Pancreatic Cancer Cells (Miapaca2) Treated With The Peptide Combination

| S. NO. | PEPTIDE COMBINATION | % Induction of Tyrosine phosphatase |
|---|---|---|
| 1 | SEQ ID NO: 4 | 15.6 ± 4.5 |
| 2 | SEQ ID NO: 3 | 14.3 ± 3.5 |
| 3 | SEQ ID NO: 2 + SEQ ID NO: 4 | 20.7 ± 2.5 |
| 4 | SEQ ID NO: 2 + SEQ ID NO: 4 + SEQ ID NO: 3 | 30.3 ± 4.0 |
| 5 | SEQ ID NO: 1 + SEQ ID NO: 2 + SEQ ID NO: 3 + SEQ ID NO: 4 | 62.0 ± 5.6 |

In Examples 8–15 the results shown are compared to the controls which e untreated cells.

EXAMPLE 8

Effect of Peptide Combination on Mitogen Activated Protein Kinase Activity

Confluent colon cancer cells (PTC) were harvested using 0.05% trypsin-0.2 mM EDTA and replated in RPMI supplemented with 10% FCS, in 6-well tissue culture plates at a density of 50,000 cells/well. After overnight incubation, the medium was changed to RPMI supplemented with 2.5% FCS. Thereafter, the cells were incubated with the peptide combination at its optimal concentration (N) for 15 minutes. The optimal concentration of the peptide combination is defined as $10^{-8}$ M concentration for SEQ ID: 1, SEQ ID: 2, SEQ ID: 3 & SEQ ID: 4. The cells were also treated with N/5 (one-fifth of the optimal concentration) and N/10 (one-tenth of the optimal concentration) of the peptide combination. The cells were washed once with lysis buffer containing 10 mM Tris/150 mM NaCl/2 mM EDTA/2 mM dithiothreitol (DTT)/1 mM orthovanadate/1 mM phenyl methyl sulfonyl fluoride (PMSF)/1% Triton-X-100 (pH=7.4). The cellular debris was precipitated at 25000 g and the supernatant retained for MAPK estimation.

The reaction was initiated by the addition of magnesium ATP buffer containing $\gamma$-$^{32}$P-ATP at a concentration of 200 µCi/microliter in presence of the substrate peptide. The mixture was incubated for 30 minutes. The reaction was terminated according to the manufacturer's instructions and the mixture was loaded on treated binding sheets, using the MAP Kinase assay kit (Amersham Pharmacia Biotech, U.S.A). The MAP Kinase activity was calculated from the rate at which phosphate group was transferred to the specific substrate peptide per minute. Table 7 below shows the inhibition of the activity of MAPK in colon cancer cells treated with various concentrations of the peptide combination.

TABLE 7

Percent Inhibition In Activity Of MAPK In Colon Cancer Cells Treated With Various Concentrations Of The Four Peptide Combination

| | MAPK activity as percent of Control values | | |
|---|---|---|---|
| Cell line | N/10 | N/5 | N |
| PTC (Colon cancer cells) | 36.2 ± 3.2 | 20.5 ± 3.1 | 10.1 ± 4.2 |

The treatment of colon carcinoma cells with SEQ ID NO:1+SEQ ID NO:2+SEQ ID NO:3+SEQ ID NO:4 was found to cause a highly significant and dose dependent downregulation of constitutive MAP Kinase activity within 15 minutes of drug treatment. The MAPK activity was reduced by 80–90% of that in the untreated cells.

EXAMPLE 9

Effect of Peptide Combination on Caspase-3 Induction

PA-1 (Ovary), MDA.MB.453 (breast), HT29 (colon) and A549 (lung) cancer cells were cultured in 25 cm² tissue culture flasks at 37° C. in a humidified incubator containing 5% $CO_2$. When cultures reached pre-confluence individual peptides of the combination and different combinations of the peptides as shown in Table 8 were added to different flasks such that the final concentration of each peptide in the flask was $10^{-8}$ M. The untreated flasks served as controls. The cells were incubated with drug for 6 hours.

After 6 hours of incubation cells were collected by trypsin treatment followed by centrifugation at 2000 r.p.m. for 10 minutes. The supernatant was gently removed and discarded and Lysis Buffer was added to the cell pellet (25 microliter of lysis buffer per 1×10⁴ cells I a 15 ml conical tube) and incubated on ice for 10 minutes and centrifuged at 10,000-×g for 1 minute. 50 microliter of supernatant(cell lysate) was transferred to the wells of a 96-well plate. 2× Reaction buffer was prepared by adding 10 microliter of fresh DTT stock per 1 ml of 2× Reaction Buffer. 50 microliter 2× Reaction Buffer was added to each well followed by addition of 5 microliter of Caspase-3 colorimetric substrate (DEVD-pNA). The plate was incubated for 1–2 hours at 37° C. Following incubation the plate was read on a microplate reader at 405 nm-wavelength light the level of caspase enzymatic activity in the cell lysate was directly proportional to the color reaction. The induction of caspase activity by the subcombinations was calculated as a percentage of control using the formula [(Sample OD/Control OD)−1]*100.

Caspase-3 activation on treatment with peptides was seen as early as 6 hours in PA-1 (ovary) cells. Table -8 shows percentage induction of caspase activity following treatment with subcombinations on cancer cell lines. The maximum caspase induction of 86.5% (PA-1), 75.9 (HT29), 68.9 (A549) and 58.6% (MDA MB 453) was seen in the four peptide combination of SEQ ID NO:1, SEQ ID NO:2, SEQ ID NO:3 and SEQ ID NO:4.

TABLE 8

Effect Of Peptide Combination On Caspase-3 Induction

| S. NO. | PEPTIDE COMBINATION | % INDUCTION | | | |
|---|---|---|---|---|---|
| | | PA-1 | MDA.MB453 | HT29 | A549 |
| 1 | SEQ ID NO: 4 | 34.8 ± 1.3 | 18.9 ± 1.0 | 18.6 ± 1.9 | 28.4 ± 2.8 |
| 2 | SEQ ID NO: 3 | 46.2 ± 2.1 | 22.8 ± 3.8 | 28.4 ± 2.4 | 38.5 ± 3.8 |
| 3 | SEQ ID NO: 2 + SEQ ID NO: 4 | 54.0 ± 3.5 | 48.2 ± 2.7 | 54.7 ± 5.3 | 46.2 ± 3.7 |
| 4 | SEQ ID NO: 2 + SEQ ID NO: 4 + SEQ ID NO: 3 | 76.1 ± 4.3 | 54.3 ± 3.2 | 67.2 ± 3.8 | 54.9 ± 4.6 |
| 5 | SEQ ID NO: 1 + SEQ ID NO: 2 + SEQ ID NO: 3 + SEQ ID NO: 4 | 86.5 ± 5.8 | 58.6 ± 3.8 | 75.9 ± 6.2 | 68.9 ± 4.7 |

EXAMPLE 10

Effect of Peptide Combination on Levels of Bcl2 Protein in Human Cancer Cells

Human adenocarcinoma cells (MiaPaCa2 (pancreatic), MCF7 (breast), PTC (colon), & squamous cells (KB, oral)) were cultured to confluence and plated in RPMI 1640 supplemented with 10% FCS, in 6-well tissue culture plates, at a density of $0.5 \times 10^6$ cells per well. The cells were incubated for 24 hours to allow complete attachment to the wells. Subsequently the media was changed to serafree RPMI and the cells incubated with the four peptide combination at its optimal concentration (N) for 20 hours (where $N=10^{-8}M$ for SEQ ID: 1, SEQ ID:2, SEQ ID:3 and SEQ ID:4 respectively). The supernatant was removed and the cells scraped and lysed at 4° C. to extract the Bcl-2 protein. Bcl-2 was quantitated by sandwich enzyme immunoassay (Oncogene Research products) according to the manufacturers instructions. As shown in Table 9, the four peptide combination reduced the expression of the antiapoptotic protein bcl2 in both the adencarcinomas and squamous carcinomas in vitro. The bcl2 levels decreased from 49–65% in vitro in different cancer cell lines in vitro.

TABLE 9

Percent decrease in levels of bcl2 protein in cancer cells treated with the peptide combination at "N" concentration.

| Cell line | Percent decrease in bcl2 levels |
|---|---|
| MiaPaCa2 | 59 ± 3.5 |
| MCF7 | 49 ± 4.0 |
| PTC | 65 ± 6.5 |
| KB | 65 ± 5.5 |

EXAMPLE 11

Effect of the Peptide Combination on the Levels of the P53 Protein in Human Cancer Cells Human adenocarcinoma cells (MiaPaCa2 (pancreatic), MCF7 (breast), Colo205 (colon), A549 (Lung) and squamous cells (KB, oral cancer) were cultured to confluence and plated in RPMI 1640 supplemented with 10% FCS, in 6-well tissue culture plates, at a density of $0.5 \times 10^6$ cells per well. The cells were incubated for 24 hours to allow complete attachment to the wells. Subsequently the media was changed to sera free RPMI & the cells incubated with the peptide combination at its optimal concentration (N) for 5 hours (where $N=10^{-8}M$ for SEQ ID:1, SEQ ID:2, SEQ ID:3 and SEQ ID:4 respectively). The supernatant was removed and the cells scraped and lysed at 4° C. to extract the wild p53 protein. P53 was quantitated by sandwich enzyme immunoassay (Rapid Format ELISA, Calbiochem) according to the manufacturers instructions.

As shown in Table 10, the four peptide combination induced the wild p53 protein both in adenocarcinomas and squamous carcinoma in vitro. The increase in the levels varied from 10–60% in different cell lines by 5 hours of drug treatment.

TABLE 10

Percent Increase In Levels Of P53 Protein In Cancer Cells Treated With The Peptide Combination

| Cell line | Percent increase in levels of p53 N |
|---|---|
| MiaPaCa2 | 10.6 ± 1.5 |
| MCF7 | 15.5 ± 2.5 |
| Colo205 | 55.8 ± 5.0 |
| A549 | 60.3 ± 5.5 |
| KB | 22.1 ± 4.0 |

EXAMPLE 12

Endothelial Cell Cytotoxicity

ECV304 and EaHy.926 cells collected at exponential growth phase were resuspended in medium ($3.3 \times 10^6$ cells/ml in RPMI 1640 containing 10% FBS). 150 microliter of medium was added to the wells of a 96-well tissue culture plate (Nunc, Denmark) followed by 30 microlieter of cell suspension. The plate was left in incubator (37° C., 5% $CO_2$) overnight. 20 microliter of the peptide combination at N, N/10 and 10N concentration (where $N=10^{-8}M$ for SEQ ID: 1, SEQ ID:2, SEQ ID:3 and SEQ ID:4 respectively) was added to marked wells of the 96-well plate. Each concentration was plated in triplicates. 20 microliter of medium alone was added to control wells while wells without cells served as blanks. A total volume of 200 microliter was ensured in each well and plate was left in incubator (37° C., 5% $CO_2$). After 72 hours of incubation an MTT assay was performed and percentage inhibition in proliferation of treated cells was calculated with respect to control cells. Table 11 shows the percent inhibition of the endothelial cells on treatment with different concentrations of the peptide combination

TABLE 11

Percent Inhibition In Proliferation Of Endothelial Cells On Treatment With Different Concentrations Of Peptide Combination

| Cell line | Percent inhibition proliferation (%) | | |
|---|---|---|---|
| | N/10 | N | 10N |
| EaHy.926 | 36.2 ± 3.2 | 44.4 ± 3.1 | 38.1 ± 4.2 |
| ECV304 | 24.1 ± 4.1 | 31.0 ± 4.6 | 28.9 ± 3.8 |

EXAMPLE 13

Anti-Migratory Activity

Polycarbonate filter transwell inserts (24 well size) with 8 micromolar pores (Nunc, Denmark) were used for the migration assay. ECV304 ($10^4$ cells/200 microliter DMEM containing 0.1% BSA) was added to the upper chamber. The lower chamber contained 600 microliter of DMEM with 0.1% BSA. The peptide combination at five different concentrations of N/100 ($10^{-10}$M), N/10 ($10^{-9}$M), N, 10N ($10^{-7}$M), and 100N ($10^{-6}$M), (where N=$10^{-8}$M for SEQ ID: 1, SEQ ID:2, SEQ ID:3 and SEQ ID:4 respectively), were added directly to the upper well and the plate incubated at 37° C. for 24 hours. The cells migrated to the lower chamber were viewed randomly at five different phase-contrast microscopic fields and total number of cells counted using Video Pro 32 Image Analysis system Table 12 shows the Percent inhibition in migration.

TABLE 12

Percent Inhibition In Migration Of Endothelial Cells After Treatment With Varying Concentrations Of The Peptide Combination

| Peptide | Percent inhibition in migration (%) | | | | |
|---|---|---|---|---|---|
| | N/100 | N/10 | N | 10 N | 100 N |
| SEQ ID: 1,<br>SEQ ID: 2,<br>SEQ ID: 3 and<br>SEQ ID: 4 | 0.00 | 93.4 ± 3.2 | 95.7 ± 2.7 | 97.3 ± 2.4 | 21.6 ± 5.2 |

EXAMPLE 14

Anti-Tube Like Structure Activity

Matrigel (350 microliter) was placed into each well of a 24-well culture plate at 4° C. and was allowed to polymerize by incubation at 37° C. for 30 min. ECV304 (1.5×$10^4$) were seeded on the Matrigel in 500 microliter DMEM supplemented with 10% FBS. Five different concentrations of N/4, N/2, N, 2.5N and 5N, (where N=$10^{-8}$M for SEQ ID:1, SEQ ID:2, SEQ ID:3 and SEQ ID:4 respectively), of peptide combination were added to the well and the plate incubated at 37° C. for 72 hours. Tube like structures formed, the length of which were individually counted at five different phase-contrast microscopic fields using Video Pro 32 Image Analysis system. Table 13 shows the percent inhibition Percent inhibition in tube length.

TABLE 13

The Tube-Like-Structure Inhibitory Activity Of The Peptide Combination At Different Concentrations

| Peptide concentration | Percent inhibition in TLS activity (%) |
|---|---|
| N/4 | 28.4 ± 3.2 |
| N/2 | 39.3 ± 4.2 |
| N | 47.0 ± 5.6 |
| 2.5 N | 42.0 ± 3.9 |
| 5 N | 58.1 ± 6.2 |

EXAMPLE 15

Effect of Peptide Combination on Vascular Endothelial Growth Factor Activity

Human adenocarcinoma cells such as MiaPaCa (Pancreas), PC3(Prostate), HT29(Colon), HuTu80 (Stomach), MDA.MB.453 (Breast), PTC (Colon), A549 (Lung) and human endothelial cells (ECV304) were plated at the density of 8–10×$10^5$ cells per 2 ml in a six well plate. After an overnight incubation of cells at 37° C., peptide combination (1N and 2N),where N=$10^{-8}$M for SEQ ID: 1, SEQ ID:2, SEQ ID:3 and SEQ ID:4 respectively, was added to the wells. The untreated wells served as controls. The plates were incubated for 4 hours at 37° C. The medium was collected from all the wells (control and treated) and spun down at 2000 r.p.m to remove the cellular material. The supernatant was collected and used for ELISA (Quantikine human VEGF, R&D Systems). The assay employs the quantitative sandwich enzyme immunoassay technique. A monoclonal antibody specific for VEGF has been pre-coated onto a microplate. Standards and samples were pipetted into the wells and VEGF present was bound by the immobilized antibody. After washing away the unbound substances, an enzyme-linked polyclonal antibody specific for VEGF was added to the wells. Following a wash to remove any unbound antibody-enzyme reagent, a substrate solution was added to the wells and color developed in proportion to the amount of VEGF bound in the initial step. The optical density of each well was determined within 30 minutes using a microplate reader set to 450 nm and reference wavelength at 540 nm.

The cells showed high levels of secretion of VEGF, which was inhibited by the addition of peptide combination. However, no significant difference was seen in inhibition at 1N and 2N concentrations of the drug. The results of the assay are summarized in the following Table 14 and depicted in the figure below.

TABLE 14

Percent Reduction In VEGF Levels In Different Tumor Types On Treatment With Peptide Combination

| | | Percent reduction in VEGF levels on treatment with peptide combination | |
|---|---|---|---|
| S. No | Cell line | 1 N | 10 N |
| 1 | HT29 (colon) | 42.1 ± 3.2 | 52.7 ± 5.3 |
| 2 | MDA.MB.453 (breast) | 38.2 ± 3.9 | 37.9 ± 2.8 |

TABLE 14-continued

Percent Reduction In VEGF Levels In Different Tumor Types On Treatment With Peptide Combination

| S. No | Cell line | Percent reduction in VEGF levels on treatment with peptide combination | |
|---|---|---|---|
| | | 1 N | 10 N |
| 3 | MiaPaCa2 (pancreas) | 36.8 ± 2.9 | 46.3 ± 4.2 |
| 4 | PC3 (prostate) | 27.7 ± 1.5 | 32.9 ± 1.2 |
| 5 | A549 (lung) | 33.2 ± 4.2 | 38.9 ± 2.1 |
| 6 | HuTu80 (stomach) | 17.6 ± 1.0 | 32.7 ± 3.2 |
| 7 | ECV304 (endothelial) | 23.9 ± 0.1 | 29.5 ± 2.9 |

EXAMPLE 16

In Vivo Anti-Tumor Activity of Peptide Combination on Primary Tumor (Colon) Xenografted Mice PTC tumor xenografts were grown in Balb/c athymic mice by subcutaneous inoculation of a single cell suspension of PTC cells ($15 \times 10^6$ cells/100 microliter). The tumor bearing animals were divided into 4 groups of three animals each including one group comprising untreated control animals. Treatment with peptide combination was initiated when the average tumor volumes, as measured using a vernier caliper, were between 400–800 mm$^3$. The peptide combination SEQ ID:2+SEQ ID:3 (in a ratio of 1:1 w/w), SEQ ID:1+SEQ ID:2+SEQ ID:3 (in a ratio of 3:1:1 w/w) and SEQ ID:1+ID:2+SEQ ID:3+SEQ ID:4 (in a ratio of 3:1:1:2 w/w) were prepared and administered to the assigned group of tumor bearing animals at a dose of 25 microgram/day (i.v followed by i.m) in two equally divided doses. The treatment was continued for a period of 14 days.

The antitumor activity of the compounds was monitored by measuring tumor volumes every fourth day using the formula W*W*L*0.4 (W=smaller diameter, L=larger diameter). The percentage inhibition of tumor growth was calculated using the formula (1−tumor volume-treated/tumor volume-control)*100. Table 15 shows the mean tumor volumes of individual groups measured till day 26 post-inoculation. FIG. 1 shows the tumor kinetics till day 26 in the treated and untreated animals. All three peptide combination showed significant antitumor activity on PTC xenografts. The percentage inhibition of tumor growth caused by SEQ ID:2+SEQ ID:3, SEQ ID:2+SEQ ID: 1+SEQ ID:3 and SEQ ID: 1+SEQ ID:2+SEQ ID:3+SEQ ID:4 as compared to controls on day 26 was 67.8%, 85.1% and 97.1% respectively.

TABLE 16

Tumor Kinetics Of Peptide Combination Treated Xenografts

| | | Tumor volume(cu.mm) | | |
|---|---|---|---|---|
| Day | Untreated | SEQID: 2 + SEQID: 3 | SEQID: 2 + SEQID: 1 + SEQID: 3 | SEQID: 1 + SEQID: 2 + SEQID: 3 + SEQID: 4 |
| 0 | 0 | 0 | 0 | 0 |
| 8 | 165.5 | 148 | 402 | 212.7 |
| 12 | 629 | 602.1 | 1208 | 976.3 |
| 16 | 2991.2 | 1536 | 1507.7 | 1508.4 |
| 20 | 5254.2 | 2470 | 1209.2 | 1159.3 |
| 27 | 7873.2 | 2530.1 | 1166.4 | 221.6 |

The invention claimed is:

1. A composition comprising a therapeutically effective combination of peptides SEQ ID NO:1 SEQ ID NO:2, SEQ ID NO:3 and SEQ ID NO:4 or a pharmaceutically acceptable salt thereof.

2. The composition as claimed in claim 1, further comprising a pharmaceutically acceptable carrier, diluent or solvent.

3. The composition as claimed in claim 1 or 2, wherein the concentration of each peptide is about $10^{-6}$ M to $10^{-10}$ M.

4. The composition as claimed in claim 1 or 2, wherein the concentration of each peptide is about $10^{-8}$ M.

5. The composition as claimed in claim 1 or 2, wherein the weight of any one peptide may vary from 1 to 3 times with respect to the weight of any of the remaining three peptides.

6. The composition as claimed in claim 1 or 2 wherein the ratio of the peptide of SEQ ID NO:1 to SEQ ID NO:2 to SEQ ID NO:3 to SEQ ID NO:4 is 3:1:1:2 w/w.

7. The composition as claimed in claim 1 or 2, wherein the weight of the peptides in a single dose is between 0.01 to 50.0 mg.

8. The composition according to claim 1 or 2, wherein a single dose is 0.05 to 500 microgram /Kg of body weight.

9. The composition according to claim 1, in the form of a tablet, lozenge, capsule, powder, aqueous or oily suspension, syrup, elixir, or aqueous solution.

10. The composition according to claim 2, in the form of a tablet, lozenge, capsule, powder, aqueous or oily suspension, syrup, elixir, or aqueous solution.

11. The composition according to claim 3, in the form of a tablet, lozenge, capsule, powder, aqueous or oily suspension, syrup, elixir, or aqueous solution.

12. The composition according to claim 4, in the form of a tablet, lozenge, capsule, powder, aqueous or oily suspension, syrup, elixir, or aqueous solution.

13. The composition according to claim 5, in the form of a tablet, lozenge, capsule, powder, aqueous or oily suspension, syrup, elixir, or aqueous solution.

14. The composition according to claim 6, in the form of a tablet, lozenge, capsule, powder, aqueous or oily suspension, syrup, elixir, or aqueous solution.

15. The composition according to claim 7, in the form of a tablet, lozenge, capsule, powder, aqueous or oily suspension, syrup, elixir, or aqueous solution.

16. The composition according to claim 8, in the form of a tablet, lozenge, capsule, powder, aqueous or oily suspension, syrup, elixir, or aqueous solution.

* * * * *

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial
<220> FEATURE:
<223> OTHER INFORMATION: This peptide was synthetically generated

<400> SEQUENCE: 1

Leu Met Tyr Pro Thr Tyr Leu Lys
1               5

<210> SEQ ID NO 2
<211> LENGTH: 8
<212> TYPE: PRT
<213> ORGANISM: Artificial
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-phenylalanine/label = D-Phe
<220> FEATURE:
<221> NAME/KEY: MISC_FEATURE
<222> LOCATION: (6)..(6)
<223> OTHER INFORMATION: /product = 2-amino-isobutyric acid/label = Aib
```

```
<400> SEQUENCE: 2

Xaa Gln Trp Ala Val Xaa His Leu
 1               5

<210> SEQ ID NO 3
<211> LENGTH: 11
<212> TYPE: PRT
<213> ORGANISM: Artificial
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-arginine/label = D-Arg
<220> FEATURE:
<221> NAME/KEY: MISC_FEATURE
<222> LOCATION: (5)..(5)
<223> OTHER INFORMATION: /product = D-phenylalanine/label = D-Phe
<220> FEATURE:
<221> NAME/KEY: MISC_FEATURE
<222> LOCATION: (7)..(7)
<223> OTHER INFORMATION: /product = D-tryptophan/label = D-Trp
<220> FEATURE:
<221> NAME/KEY: MISC_FEATURE
<222> LOCATION: (9)..(9)
<223> OTHER INFORMATION: /product = D-tryptophan/label = D-Trp
<220> FEATURE:
<221> NAME/KEY: MISC_FEATURE
<222> LOCATION: (11)..(11)
<223> OTHER INFORMATION: /product = Aminocyclopentance carboxylic acid/
                        label = Ac5c

<400> SEQUENCE: 3

Xaa Pro Lys Pro Xaa Gln Xaa Phe Xaa Leu Xaa
 1               5                   10

<210> SEQ ID NO 4
<211> LENGTH: 8
<212> TYPE: PRT
<213> ORGANISM: Artificial
<220> FEATURE:
<223> OTHER INFORMATION: This peptide was synthetically generated
<220> FEATURE:
<221> NAME/KEY: MISC_FEATURE
<222> LOCATION: (1)..(1)
<223> OTHER INFORMATION: /product = D-phenylalanine/label = D-Phe
<220> FEATURE:
<221> NAME/KEY: MISC_FEATURE
<222> LOCATION: (4)..(4)
<223> OTHER INFORMATION: /product = D-tryptophan/label = D-Trp
<220> FEATURE:
<221> NAME/KEY: MISC_FEATURE
<222> LOCATION: (5)..(5)
<223> OTHER INFORMATION: /product = Ornithine/label = Orn
<220> FEATURE:
<221> NAME/KEY: MISC_FEATURE
<222> LOCATION: (7)..(7)
<223> OTHER INFORMATION: /product = Penicillamine/label = Pen

<400> SEQUENCE: 4

Xaa Cys Tyr Xaa Xaa Thr Xaa Thr
 1               5
```